(12) United States Patent
Ben Haim et al.

(10) Patent No.: US 12,358,917 B2
(45) Date of Patent: Jul. 15, 2025

(54) PROCESSES AND INTERMEDIATES FOR PREPARING A Btk INHIBITOR

(71) Applicant: Janssen Pharmaceutica NV, Beerse (BE)

(72) Inventors: Cyril Ben Haim, Vosselaar (BE); Thomas Joost Martti Michiels, Leiden (NL); Florian Damien Medina, Brussels (BE); Simon Albert Wagschal, Schaffhausen (CH); Dominique Paul M. Depré, Hamme-Mille (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/719,607

(22) Filed: Apr. 13, 2022

(65) Prior Publication Data

US 2023/0107573 A1    Apr. 6, 2023

Related U.S. Application Data

(63) Continuation of application No. 16/339,805, filed as application No. PCT/EP2017/075289 on Oct. 5, 2017, now abandoned.

(30) Foreign Application Priority Data

Oct. 6, 2016    (EP) .................................. 16192603

(51) Int. Cl.
C07D 473/32    (2006.01)
C07B 55/00    (2006.01)

(52) U.S. Cl.
CPC ............ C07D 473/32 (2013.01); C07B 55/00 (2013.01)

(58) Field of Classification Search
CPC .................................................. C07D 473/32
See application file for complete search history.

(56) References Cited

U.S. PATENT DOCUMENTS 7,514,444 B2 *  4/2009  Honigberg ............... A61P 19/02
                                                    514/263.22

FOREIGN PATENT DOCUMENTS

| JP | 2001-002637 A | 1/2001 |
|---|---|---|
| WO | 2008/039218 A2 | 4/2008 |
| WO | 2008/121742 A2 | 10/2008 |
| WO | 2011/153514 A2 | 12/2011 |
| WO | 2013/184572 A1 | 12/2013 |
| WO | 2016/141068 A1 | 9/2016 |
| WO | 2016/164404 A1 | 10/2016 |
| WO | 2017/125423 A1 | 7/2017 |
| WO | 2017/125424 A1 | 7/2017 |

OTHER PUBLICATIONS

Ju, Organic Process Research and Development, 2014, vol. 18(6), pp. 827-830.*
Bartlett "Exploiting Chemical Diversity for Drug Discovery" Edited by Paul A Bartlett and Michael Entzeroth, The Royal Society of Chemistry, 2006, pp. 113-118.*
"Find ETDs Home > Thesis Resources > Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
Registry/Zregistry (Cas Registrysm) Sep. 2016 2 pages.*
Kikuchi, Journal of Labelled Compounds & Radiopharmaceuticals, 44(1), 31-41; 2001.*
Carvalho, Int. J. Mol. Sci. 2015, 16, 29682-29716.*
Rosenberg, Zcomm.org. Consumer Drug Ads, Apr. 11, 2019.*
Barnes, Blood Advances, 2018, 2(15), 1946-1956.*
Kim, Current Opinion in Biotechnology 2003, 14:131, 578-587.*
Dow, Practical Methods for Biocatalysis and Biotransformations 2 (2012), 203-206.*
Parvulescu, Topics in Catalysis (2010), 53(13-14), 931-941.*
Kim, Curr Opin Biotechnol Dec. 2002; 13(6):578-87.*
Barnes, "Cost-effectiveness of ibrutinib as first-line therapy for chronic lymphocytic leukemia in older adults without deletion 17p", Blood Advances, 2018, vol. 2(15), pp. 1946-1956.
Boren, "(S)-Selective Kinetic Resolution and Chemoenzymatic Dynamic Kinetic Resolution of Secondary Alcohols", Chem. Eur. J., 2006, vol. 12, pp. 225-232.
Carvalho, "Recent Advances in Lipase-Mediated Preparation of Pharmaceuticals and Their Intermediates", Int. J. Mol. Sci., 2015, vol. 16, pp. 29682-29716.
Giorgio et al., "Preparation of enantiomerically pure N-heterocyclic amino alcohols by enzymatic kinetic resolution", Tetrahedron Asymmetry, May 12, 2015, vol. 26, No. 12, pp. 638-643.
Honig et al., "Enzymic resolutions of heterocyclic alcohols", Biocatalysis, Jul. 11, 2019, vol. 9(14), pp. 61-69.
Horwood et al., "Bruton's Tyrosine Kinase Is Required For Lipopolysaccharide-induced Tumor Necrosis Factor a Production", The Journal of Experimental Medicine, 2003, vol. 197, pp. 1603-1611.
Iwaki et al., "Btk plays a crucial role in the amplification of Fc?RI-mediated mast cell activation by kit", Journal of Biological Chemistry, 2005, vol. 280(48), pp. 40261-40270.

(Continued)

*Primary Examiner* — Nizal S Chandrakumar
(74) *Attorney, Agent, or Firm* — BakerHostetler

(57) ABSTRACT

Disclosed is a process for the preparation of certain intermediates, e.g. the following compound:

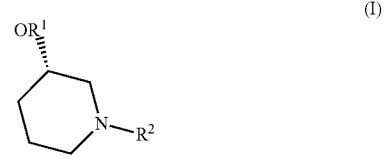

which intermediate and processes are useful in the preparation of a BTK inhibitor, such as ibrutinib.

18 Claims, No Drawings

(56) References Cited

OTHER PUBLICATIONS

Jeffries et al., "Bruton's Tyrosine Kinase Is a Toll/Interleukin-1 Receptor Domain-binding Protein That Participates in Nuclear Factor ?B Activation by Toll-like Receptor 4", Journal of Biological Chemistry, 2003, vol. 278, pp. 26258-26264.

Ju et al., "Development of a Biocatalytic Process to Prepare (S)-N-Boc-3- hydroxypiperidine", Organic Process Research and Development, 2014, vol. 18(6), pp. 827-830.

Kikuchi et al., "Synthesis of piperdinyl and pyrrolidinyl butyrates for potentional In Vivo measurement of cerebral butyrylcholinesterase activity", Journal of Labelled Compounds and radiopharmaceuticals, Jan. 1, 2021, vol. 44, No. 1, pp. 31-41.

Kim, "(S)-Selective Dynamic Kinetic Resolution of Secondary Alcohols by the Combination of Subtilisin and an Aminocyclopentadienylruthenium Complex as the Catalysts", J. Am. Chem. Soc., 2003, vol. 125, pp. 11494-11495.

Kim, "Boron-Directed Regio- and Stereoselective Enyne Cross Metathesis:? Efficient Synthesis of Vinyl Boronate Containing 1,3-Dienes", Org. Lett., 2005, vol. 7, No. 20.

Kim, Current Opinion in Biotechnology, 2003, vol. 14(131), pp. 578-587.

Koeller et al., "Enzymes for chemical synthesis", Nature, 2001, vol. 409, pp. 232-240.

Kurosaki, "The Invention Bruton's tyrosine kinase (Btk), a member of the Tec family of non-receptor tyrosine kinases, is a key signaling enzyme expressed in all", Curr. Op. Imm., 2000, pp. 276-281.

Lihammar et al., "An efficient dynamic kinetic resolution of N-Heterocylic 1,2-Amino Alcohols", Advanced Synthesis & Catalysis, Sep. 26, 2011, vol. 353, No. 13, pp. 2321-2327.

Quek et al., "A role for Bruton's tyrosine kinase (Btk) in platelet activation by collagen", Current Biology, 1998, vol. 8(20), pp. 1137-1140.

Schaeffer et al., "Tee family kinases in lymphocyte signaling and function", Curr. Op. Imm, 2000, pp. 282-288.

Tomori et al., "Lipase-catalyzed practical synthesis of (R)-1-Benzyl-3-Hydroxy-2.5-Pyrralidinedion E and its related compounds", Bulletin of the chemical society of Japan, Jan. 1, 1996, vol. 69, No. 1, pp. 207-215.

Vassilev et al., "Bruton's tyrosine kinase as an inhibitor of the Fas/CD95 death-inducing signaling complex", Journal of Biological Chemistry, 1999, vol. 274(3), pp. 1646-1656.

* cited by examiner

PROCESSES AND INTERMEDIATES FOR PREPARING A Btk INHIBITOR

This application is a continuation of U.S. patent application Ser. No. 16/339,805, filed Apr. 5, 2019, which is a U.S. national stage application of International Patent Application No. PCT/EP2017/075289, filed Oct. 5, 2017, which claims priority to European Patent Application No. 16192603.5, filed Oct. 6, 2016.

FIELD OF THE INVENTION

The present invention relates to synthesis procedures and synthesis intermediates of substituted bicyclic compounds, especially compounds that are useful as medicaments, for instance Bruton's tyrosine kinase (Btk) inhibitors such as ibrutinib.

BACKGROUND OF THE INVENTION

Ibrutinib is an organic small molecule having IUPAC name 1-[(3R)-3-[4-amino-3-(4-phenoxyphenyl)pyrazolo[3,4-d]pyrimidin-1-yl]piperidin-1-yl]prop-2-en-1-one. It is described in a number of published documents, including international patent application WO 2008/039218 (Example 1b), and is described as an irreversible inhibitor of Btk.

Btk plays an essential role in the B-cell signaling pathway linking cell surface B-cell receptor stimulation to downstream intracellular responses. Btk is a key regulator of B-call development, activation, signaling, and survival (Kurosaki, *Curr Op Imm,* 2000, 276-281; Schaeffer and Schwartzberg, *Curr Op Imm* 2000, 282-288). In addition, Btk plays a role in a number of other hematopoetic cell signaling pathways, e.g. Toll like receptor (TLR) and cytokine receptor-mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. See e.g., C. A. Jeffries, et al., (2003), *Journal of Biological Chemistry* 278:26258-26264; N. J. Horwood, et al., (2003), *The Journal of Experimental Medicine* 197:1603-1611; Iwaki et al. (2005), *Journal of Biological Chemistry* 280 (48):40261-40270; Vassilev et al. (1999), *Journal of Biological Chemistry* 274(3):1646-1656, and Quek et al (1998), *Current Biology* 8(20):1137-1140.

Ibrutinib has been approved for certain hematological malignancies in several countries including the US and the EU, and is also being studied in clinical trials for other hematological malignancies. Such malignancies include chronic lymphocytic leukemia, mantle cell lymphoma, diffuse large B-cell lymphoma and multiple myeloma.

The synthesis of ibrutinib makes use of a chiral hydroxypiperidine. It is an object of the present invention to find an alternative and/or improved process for obtaining a chiral hydroxypiperidine, and such a compound may be used as intermediate or building block in the synthesis of ibrutinib. One known method to prepare a chiral hydroxypiperidine is described e.g. by Ju et al, *Org. Process Res. Dev.,* 2014, 18 (6), pp 827-830, where a biocatalytic process is employed to reduce the corresponding ketone using KRED (and NADH/NAD).

Various strategies may be used for introduction of chiral centres, including enzymatic strategies. For instance, various enzymes may be used to promote kinetic resolutions (and can be referred to as enzymatic kinetic resolutions). For such processes, the maximum theoretical yield would be 50% given the conversion of only one of the enantiomers in the racemate. However, dynamic kinetic resolutions may overcome the yield limitation by racemising the remaining unreacted enantiomer enabling more complete conversion yields. A number of catalysts may fulfil this role, for instance organometallic catalysts such as ruthenium complex catalysts, some of which may be known.

Several further documents disclose enzymatic resolution processes, including for example Hönig et al, Biocatalysis, 1994, vol 9, pp 61-69 "Enzymatic Resolutions of Heterocyclic Alcohols", Tatsuya Kikuchi et al, *J. Labelled Cpd. Radiopharm.* 44, 31-41 (2001), Lihammar et al, *Adv. Synth. Catal.* 2011, 353, 2321-2317 and patent document JP2001002637.

However, such documents only disclose enzymatic processes resulting in a particular stereochemistry or configuration of end product. For instance, the Hönig article discloses resolution of some heterocyclic alcohols using enzymes. Specifically, a 1-methyl-hydroxy-piperidine ring is first converted via a transesterification reaction to an acetate, and thereafter an enzymatic hydrolysis reaction proceeded with a varying degree of success. This document does not disclose an enzymatic kinetic acylation reaction. The Tatsuya Kikuchi article discloses for example, a Boc-protected hydroxy-piperidine that undergoes a kinetic resolution mediated via an enzymatic acylation reaction with vinyl acetate and where the enzyme is a lipase. Such reaction proceeds with a certain stereochemistry, namely the (R)-configuration at the relevant chiral centre bearing the —OAc group. The Lihammar journal article also discloses for example a 1-N-substituted hydroxy-piperidine which undergoes a kinetic resolution under enzymatic conditions in an acylation reaction, again forming the corresponding compound with an (R)-configuration at the chiral centre. Finally, JP 2001002637 discloses only enantiomerically-enriched N-substituted pyrrolidine rings; further such optically active compounds are prepared from chiral precursors in a stereospecific reaction, rather than via an enzymatic kinetic resolution process.

DESCRIPTION OF THE INVENTION

There is now provided a process for preparing a compound of formula (I)

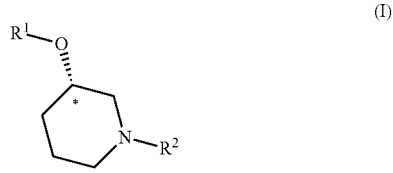

in an enantioenriched form,
wherein
$R^1$ represents hydrogen or an acyl group;
$R^2$ represents hydrogen or an amino-protecting group;
* represents a chiral centre of an (S) configuration;

which comprises enzymatic kinetic resolution of a compound of formula (II)

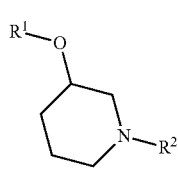

(II)

wherein

R¹ represents hydrogen and R² is as defined above, and the process is performed in the presence of an acyl donor, which process may be referred to herein as a process of the invention (which consists of one or more embodiments).

The process of the invention produces an enantioenriched compound of formula (I) and may alternatively be described as a process for preparing a composition comprising compound of formula (I) in which the (S)-enantiomer is the predominantly formed enantiomer, thus providing an ee of greater than 20% (and in embodiments described herein in an ee greater still).

The advantages of the present invention, and indeed the differences with what was previously disclosed, reside in the selectivity of the conversion to the desired optically-active product and also its degree of conversion.

For the avoidance of doubt, the compound of formula (II) starting material is racemic (or of low enantiopurity, e.g. displaying an enantiomeric excess "ee" of less than 20%) i.e. the chiral centre at the point of attachment of the —OR¹ group contains an equimolar mixture of (R)- and (S)-configurations (or a substantially lower preference for one configuration compared to the other, e.g. less than 60% of the dominant enantiomer). Whereas the corresponding chiral centre of the compound of formula (I) is mainly of the (S)-configuration (and is described as being an "enantioenriched product").

It is mentioned that the process of the invention is an enzymatic resolution. Hence, the process of the invention is performed in the presence of a suitable enzyme (that affects the resolution, i.e. that selectively reacts with one of the two enantiomers of the racemate of formula (II)). Suitable enzymes may accompany the acyl donor and are discussed hereinafter.

In an embodiment, the process of the invention is a dynamic kinetic resolution, in which case the process of the reaction is further performed in the presence of a racemisation catalyst. For instance any one or more of the following racemisation catalysts may be employed:

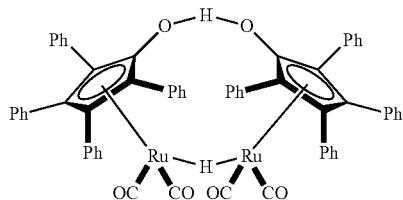

I

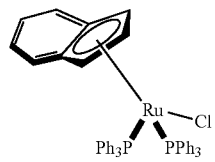

II

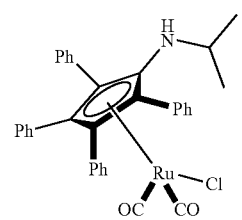

III

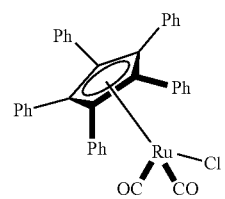

IV

Unless otherwise specified, alkyl groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl groups may also be part cyclic/acyclic. Such alkyl groups may also be saturated or, when there is a sufficient number (i.e. a minimum of two) of carbon atoms, be unsaturated (including therefore e.g. "vinyl" moieties).

In the process of the invention, the R¹ or R² integer of the compound of formula (II) need not be the same as the corresponding integers of the compound of formula (I). Hence, the R¹ moiety of compound (II) may be hydrogen, but during the course of the process of the invention, such group may be converted to an acyl group (in the compound of formula (I)) for instance when the enzyme is employed along with an acyl donor. However, further encompassed within the scope of the process of the invention is the situation where the compound of formula (I) in which R¹ is acyl is saponificated to a further compound of formula (I) in which R¹ is hydrogen. Similarly, the R² integer in the conversion from compound (II) to (I) may be the same (e.g. a protecting group, such as a tert-butoxycarbonyl (Boc-group)) or different. For instance, the R² nitrogen-protecting group may be necessary on the compound of formula (II) during the course of the process of the invention and it may therefore carry over to the resultant compound of formula (I). However, thereafter, the protecting group may be removed (i.e. deprotected) to provide a compound of formula (I) in which R² represents hydrogen. If downstream chemistry is intended (e.g. as described hereinbelow), then, in an embodiment, R² represents a protecting group (e.g. Boc) and the compound of formula (I) in which R² represents Boc is converted to a downstream product, for examples as described hereinbelow.

In the process of the invention, given that the compound of formula (II) is reacted in the presence of an acyl donor (and R¹ is hydrogen), such an acyl group may then, during the process, result in being attached to the —OH group and hence forming a —O-acyl moiety (i.e. a compound of formula (I) in which R¹ represent "acyl"; which for the purposes of this invention is encompassed within the definition of "protecting group" as defined herein). Hence $R^1$ may represent —C(O)—$C_{1-8}$ alkyl (in which the alkyl moiety is optionally substituted by one or more substituents selected from e.g. halo (e.g. fluoro), —$OC_{1-6}$ alkyl (e.g. methoxy; itself optionally substituted by one or more fluoro atoms) and phenyl (itself optionally substituted by one or more substituents selected from halo and $C_{1-3}$ alkyl)) or —C(O)-phenyl (in which the phenyl is optionally substituted by one or more substituents selected from e.g. halo and $C_{1-3}$ alkyl), and $R^1$ may form, for example, a —C(O)CH$_2$—OCH$_3$ moiety or a —C(O)CH$_2$CH$_2$CH$_3$ moiety (in an embodiment the $R^1$ acyl moiety represents —C(O)CH$_2$CH$_2$CH$_3$). The acyl donor, in an embodiment, may represent a compound of the following formula $R^x$—$R^1$, in which $R^1$ is as hereinbefore defined, and $R^x$ represents —O—$C_{1-8}$ alkyl (optionally substituted by one or more substituents selected from fluoro and —$OC_{1-6}$ alkyl; the latter alkyl moiety optionally substituted by one or more fluoro atoms) or —O-phenyl (optionally substituted by one or more substituents selected from halo (e.g. chloro, fluoro, bromo), —NO$_2$, $C_{1-6}$ alkyl and —$OC_{1-6}$ alkyl; in which the latter two alkyl moieties are themselves optionally substituted by one or more fluoro atom). The possible substituents on the "phenyl" moiety may be attached at any position (e.g. at the para-position). In an embodiment, the "acyl donor" represents a butyrate, e.g. a compound in which $R^1$ represents —C(O)—CH$_2$CH$_2$CH$_3$ (which is thus the acyl moiety in the resultant compound of formula (I)) and in which $R^x$ represents a suitable moiety (e.g. as herein defined) but which in which in an embodiment, it represents —O—$C_{1-6}$ alkyl (e.g. —$OC_{1-3}$ alkyl) optionally substituted by one or more fluoro atoms, so forming e.g. a —O—CH$_2$—CF$_3$ moiety. In an aspect, therefore, the acyl donor is 2,2,2-trifluoroethyl butyrate or 4-fluorophenyl butyrate.

Protecting groups that may be mentioned may be described as follows:

It is further indicated above that $R^2$ is a nitrogen protecting group. Such groups include those that result in the formation of:
- an amide (e.g. N-acetyl)
- optionally substituted N-alkyl (e.g. N-allyl or optionally substituted N-benzyl)
- N-sulfonyl (e.g. optionally substituted N-benzenesulfonyl)
- a carbamate
- a urea
- trityl (triphenylmethyl), diphenylmethyl, or the like Hence, $R^2$ may represent:
- —C(O)$R^{r1}$ (in which $R^{r1}$ may represent $C_{1-6}$ alkyl or optionally substituted aryl); $C_{1-6}$ alkyl, which alkyl group is optionally substituted by one or more substituents selected from optionally substituted aryl (e.g. may form a benzyl moiety);
- —S(O)$_2R^{r2}$ (in which $R^{r2}$ may represent optionally substituted aryl); or, in an embodiment, —C(O)O$R^{r3}$ (in which $R^{r3}$ may represent optionally substituted aryl or, in a further embodiment, optionally substituted $C_{1-6}$ (e.g. $C_{1-4}$) alkyl, e.g. tert-butyl (so forming, for example, a tert-butoxycarbonyl protecting group, i.e. when taken together with the amino moiety, a tert-butylcarbamate group) or a —CH$_2$phenyl group (so forming a carboxybenzyl protecting group));
- —C(O)N($R^{r4}$)$R^{r5}$ (in which, in an embodiment, $R^{r4}$ and $R^{r5}$ independently represent hydrogen, $C_{1-6}$ alkyl, optionally substituted aryl or —C(O)$R^{r6}$, and $R^{r6}$ represents $C_{1-6}$ alkyl or optionally substituted aryl).

In an embodiment, $R^2$ represents —C(O)O$R^{r3}$ (in which $R^{r3}$ may represent $C_{1-6}$ alkyl, e.g. tert-butyl) and, hence, in an aspect, the $R^2$ protecting group is tert-butoxycarbonyl (also known as, and referred to herein, as a BOC or Boc group).

The process of the invention produces enantioenriched forms or products, by which we mean the products produced have an enantiomeric excess of greater than 20%, for instance greater than 40%, such as more than 60% and, in an embodiment, greater than 80% enantiomeric excess. The enantioenriched products may even be greater than 90% (for example, they may consist essentially of a single enantiomer, by which we mean that the ee may be 95% or higher, e.g. above 98% or about 100%). Such enantioenrichment (or ees) may be obtained directly, or through further purification techniques that are known to those skilled in the art. For instance, the process of the invention may produce a compound of formula (I) in which $R^1$ represents H or an acyl group, wherein such a product is enantioenriched.

Where equivalents are referred to, for the avoidance of doubt, this is intended to mean molar equivalents.

In an embodiment, the enzymatic kinetic resolution (e.g. dynamic kinetic resolution) is performed in the presence of an enzyme and an acyl donor.

The enzyme is suitable to effect the desired resolution, i.e. to selectively react with one of the two enantiomers in the racemate of formula (II) to provide the compound of formula (I) (i.e. a product that is enantioenriched).

Various screening methods may be used to identify an enzyme that is suitable for the stereoselective kinetic resolution. Suitable enzymes can be identified by screening available enzymes, e.g. using high throughput screening techniques or by using enrichment isolation techniques. In such enrichment isolation techniques carbon-limited or nitrogen-limited media can be supplemented with an enrichment substrate. The enzymes giving the best results can be further selected by further experimentation (e.g. using the conditions described herein, performing the process of the invention as described herein). The properties of the enzymes can be further enhanced by enzyme engineering. For example, enzyme engineering can be employed to improve the reaction rate, the yield and the selectivity of the reaction, in particular the enantioselectivity. Furthermore, enzyme engineering can be used to broaden the pH and temperature range at which the enzymes can be employed as well as their tolerance to certain solvents. Enzyme engineering techniques which can be employed include rational design methods, such as site-directed mutagenesis and in-vitro-directed evolution techniques. Such techniques are described e.g. in K. M. Koeller and C. H. Wong, "Enzymes for chemical synthesis", Nature, 409: 232-240 and the references cited therein, which are incorporated herein by reference.

The enzyme can be used in the form of a crude lysate or in a purified form. Alternatively, the enzyme can be immobilized and used as such. Immobilization techniques are known to a person skilled in the art. Useful solid supports include, e.g. polymer matrices such as calcium alginate, polyacrylamide, Eupergit®, and other polymeric materials, as well as inorganic matrices, such as Celite®. Immobilization techniques are advantageous because the enzyme and the product can be easily separated. Additionally, the immobilized enzyme may be recycled and reused rendering the process more economic. Other techniques such as cross-linked enzyme aggregates (CLEAs) or cross-linked enzyme crystals (CLECs) are also applicable in the present invention.

Certain enzymes which have been found to be suitable for use in the present invention include proteases and lipases. Suitable enzymes gave, in the process of the invention, enantioenriched product of formula (I), e.g. a product with an ee of greater than 20%.

The enzyme may be a protease (e.g. a non-specific protease) for instance a serine protease. In an embodiment, it may be a subtilase such as a subtilisin (which may be obtained from *Bacillus subtilis*, or from certain types of soil bacteria, for example *Bacillus amyloliquefaciens*. In an embodiment, the enzyme is a protease that is Subtilisin. Subtilisin may also be referred to by several other names, including inter alia alcalase and savinase (and can depend on a commercial source from which it is obtained). In another embodiment, the enzyme is an alkaline protease, such as alkaline protease B. In another embodiment, the enzyme is lipase from *Carica papaya* (or from *papaya* latex). In another embodiment, the enzyme is Papain, protease from *papaya latex*.

The enzyme may be also be a lipase. For instance it may be a lipase that is expressed and secreted by pathogenic organisms. In an embodiment, the lipase may be Lipase A from *Candida rugosa*, Lipase B from *Candida rugosa* and/or Lipase from *Carica papaya*.

The process of the reaction may also be carried out in the presence of a phosphate buffer for hydrolysis.

For instance, the enzymatic process may be one in which the enzyme is selected from:
Savinase (e.g. commercially available from ChiralVision; also referred to as "SAV")—from the protease group
*Candida rugosa* lipase B (e.g. commercially available from Almac, for instance article AH24 and/or article AH09)
*Candida rugosa* lipase A (e.g. commercially available from Almac, for instance article AH06)
Lipase from *Carica papaya* (e.g. commercially available from Almac, for instance article AH17)
alkaline Protease B (e.g. commercially available from Almac, for instance article AH19)
Subtilisin (e.g. commercially available from Almac)

The use of such enzymes favours the selectivity of the process of the invention such that the (S)-configuration is predominantly produced (in favour of the (R)-configuration). Positive ees can be obtained for any of these enzymes and in an aspect the enzyme is Subtilisin or Savinase (and, in particular, Savinase commercially available from ChiralVision; also referred to herein as "SAV").

Regarding the specific enzymes from commercial sources mentioned above, more detail may be obtained from the supplier, for instance in the case of Savinase from ChiralVision (also referred to as "Savinase, Subtilisin"), this a protease from *Bacillus* sp. (e.g. covalent on acrylic beads) with activity of 750 ELU/g (where ELU refers to Enzyme-Linked Immunosorbent unit; and 1 ELU unit=1 μmol lactic acid (ethyl lactate hydrolysis) released per minute/g immobilized enzyme at 25 C and pH 6.8).

A suitable quantity of enzyme may be employed in the process of the invention, and it may be dependent on the specific enzyme chosen. However, the process of the invention is, in an aspect, performed in the presence of about 1 and 100 g/mol (e.g. between about 10 and 50 g/mol, e.g. about 25 g/mol). In an embodiment, these quantities are particularly employed when e.g. the Savinase catalyst is employed. In this instance "per mol" refers to per mol of the compound of formula (II).

In an embodiment, the enzymatic kinetic resolution (e.g. dynamic kinetic resolution) is performed in the presence of an enzyme and an acyl donor, in which the acyl donor is selected from:
acetyl donors (such as isopropenyl acetate, phenyl acetate, and the like)
butyrate donors (such as isopropyl butyrate, 2,2,2-trifluoroethyl butyrate (TFEB), vinyl butyrate, and the like)

In an embodiment, the acyl donors are the butyrate donors, as these advantageously may lead (in certain instances) to an improvement in ee and/or improvement in yield conversion, for instance as shown in the experimental.

Percentage conversion of the process of the invention (and percentage ee of the desired product) may increase depending on the acyl donor used and/or the solvent (or conditions) employed. In an embodiment percentage conversion may be greater than 10%, for instance greater than 20%, e.g. greater than 30% (in an embodiment, about 50%, or in a further embodiment greater than 50%) and/or percentage ee in an embodiment is greater than 30%, for instance greater than 50%, e.g. greater than 70% (in an embodiment, greater than 90%, such as greater than 95% or about 100%).

In the process of the invention at least one acyl donor equivalent is employed compared to the compound of formula (II). In an aspect, at least 1.5 equivalents is employed (compared to the compound of formula (II)). For instance about two equivalents are employed (or at least two equivalents). In an embodiment less than four (e.g. less than three) equivalents are employed, which may have the advantage that the process of the invention does not result in a decrease (or degradation) of cc.

Advantageously, when the kinetic resolution process of the invention is performed in the presence of the savinase enzyme and a butyrate acyl donor, then ee can be greater than 50% (e.g. greater than 60%, such as greater than 75% and in an aspect, greater than 90%, e.g. greater than 95% ee) and/or the conversion can be greater than 5% (e.g. greater than 10%, greater than 20% or 30% and in an embodiment greater than 50%). The highest conversion may be obtained when vinyl butyrate is employed.

In an embodiment the process of the invention is performed in the presence of a base such as an organic or inorganic base. Such bases that may be employed include carbonate bases (e.g. sodium carbonate, calcium carbonate, barium carbonate, cesium carbonate, potassium carbonate and the like), hydroxide bases (e.g. potassium hydroxide, lithium hydroxide, magnesium hydroxide and the like), alkoxide bases (e.g. tert-butoxides, such as potassium tert-butoxide), amine bases (e.g. trialkylamine, such as triethylamine, dimethylaminopyridine (DMAP), and the like), amide bases (e.g. LDA or LiHMDS, i.e. lithium diisopropylamide or lithium bis(trimethylsilyl)amide) or other suitable bases (or mixtures of bases). In an embodiment the base employed is an inorganic base (e.g. sodium carbonate).

In an embodiment, there is at least 0.25 base equivalents employed (the base may be one base or a mixture of more than one, e.g. two, different bases) compared to the compound of formula (II). In an embodiment, there is at least about 0.5 equivalents of base (which has the advantage that even such an amount can significantly increase the reaction speed). In an embodiment, there is either about 1, 2, 3 or 4 equivalents of base employed (compared to the compound of formula (II)). With 2 equivalents (or more) of base, only a slight increase in conversion may be observed. Hence, in an embodiment between about 0.5 and 1.5 (e.g. about 1) equivalents of base (e.g. an inorganic base, such as a carbonate, e.g. sodium carbonate) are employed. It may be seen that different bases may result in differing reaction efficiency and/or differing yields and or purity of the desired product.

The process of the invention is, in an embodiment, performed in the presence of a suitable solvent. Suitable solvents include solvents such as aromatic solvents (e.g. toluene, pyridine), ethers (e.g. dioxane, THF (tetrahydrofuran), EtOAc (ethyl acetate), methyl ter-butyl ether, 2-methyltetrahydrofuran), alcohols (e.g. propanol, tert-amyl alcohol), alkanes (e.g. heptane, cyclohexane) and the like. In an embodiment, the solvents will be those that effect the highest conversion while keeping the ee high. The aforementioned alcohols all contributed to ensuring that the product (compound of formula (I)) obtained by the process of the invention maintained a high ee (in an embodiment, greater than 90%) In an embodiment, the solvent for use in the process of the invention may be toluene or methyl-THF. Such solvents may have the advantage that they achieve the fastest conversion (and maintain high ee; e.g. as described herein). For instance, reaction of a compound of formula (II) in which $R^2$ is Boc and $R^1$ is hydrogen, using Savinase as the enzyme (25 g/mol), DIPEA as the base (1 equiv compared to compound of formula (01)), vinyl butyrate as the acyl donor (2 equivs compared to the compound of formula (II)) and using solvent in a dilution of 1 L/mol at a reaction temperature of 30° C., different solvents gave different conversion (and different rates of conversion): toluene in this instance gave a conversion of more than 20% in 10 hours and a conversion of over 50% in 50 hours (and maintained an ee of 94.8% for the desired product of formula (I) in which $R^2$ is Boc and $R^1$ is —C(O)—$C_3H_7$); Me-THF in this instance gave a conversion of about 15% in 10 hours and a conversion of above 40% (but less than 50%) in 50 hours (maintaining an ee of the same desired product of 97.2%).

For the process of the invention to be carried out in the instance where a solvent is employed, then the ratio of the solvent per mol of compound of formula (I) should be reasonable to ensure that the conversion of compound of formula (II) to compound of formula (I) is efficiently effected. For instance, a suitable amount of solvent may be between about 0.25 L/mol (compared to mol of compound of formula (II)) and 6 L/mol (for instance between about 0.25 L/mol and 4 L/mol). In an embodiment, between about 0.5 L/mol and 1.5 L/mol (e.g. about 1 L/mol) solvent is employed.

The reaction temperature of the process of the invention is, in an embodiment, between about 0° C. and about 60° C., but is dependent on how the temperature affects the ee of the final product (balanced with the increase in conversion that an increase in temperature may have). For instance, in an embodiment, the temperature is kept below about 50° C. as higher temperatures may result in a decrease (or degradation) of ee. In a further embodiment, the temperature is kept above room temperature (e.g. above about 25° C.) as that may have a positive effect on the reaction rate and, particularly, on the conversion. In an embodiment, the process of the invention is performed at a temperature of between about 25 and 40° C. (e.g. between about 25 and 35° C.), such as at about 30° C.

The process of the invention may also be allowed to react for a suitable period of time. For instance the progress of the reaction may be monitored (e.g. by thin layer chromatography) and the duration may be for a period of between about 1 hour and about 72 hours. In an embodiment the reaction time may be between about 12 hours and about 48 hours (for instance between about 16 and 48 hours, such as between 24 and 48 hours e.g. about 40 hours).

The result of the process of the invention is in fact a kinetic resolution, conditions for which are discussed herein. In the case where the kinetic resolution is not a dynamic kinetic resolution, then any undesired product (e.g. unreacted started material) may be removed or separated using standard conditions.

In a further aspect of the invention, there is provided a process for separating the product obtained (compound of formula (I)) from the process of the invention (which may be referred to herein as the "compound of the invention"). The compound of the invention (or product obtained by the process of the invention) may thus be separated/isolated. This may be achieved in several ways:

flash column chromatography
precipitation/crystallisation
derivatisation, optionally followed by precipitation/crystallisation
extraction (e.g. derivatisation followed by extraction)
distillation In an aspect, the method is derivatisation, for example where the undesired product (e.g. unreacted starting material) is derivatised (e.g. by reaction with succinic anhydride, so forming a group with a terminal carboxylic acid moiety), which may allow for possible separation, extraction or isolation (e.g. the carboxylic acid may be removed in the work-up procedure).

In further embodiments of the invention, there is provided a process of the invention as described herein, following by yet further process steps.

The compound of formula (I) (in enantioenriched form) may be used in the preparation of further compounds, for example further pharmaceutical products (or intermediates thereto) such as pharmaceutical products that are useful in the treatment of cancer (such as hematological malignancies), and particularly the pharmaceutical product may be ibrutinib.

Ibrutinib may be prepared in WO 2008/039218 (Example 1b) in accordance with the following scheme:

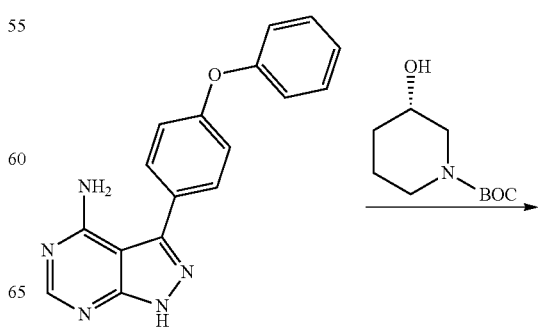

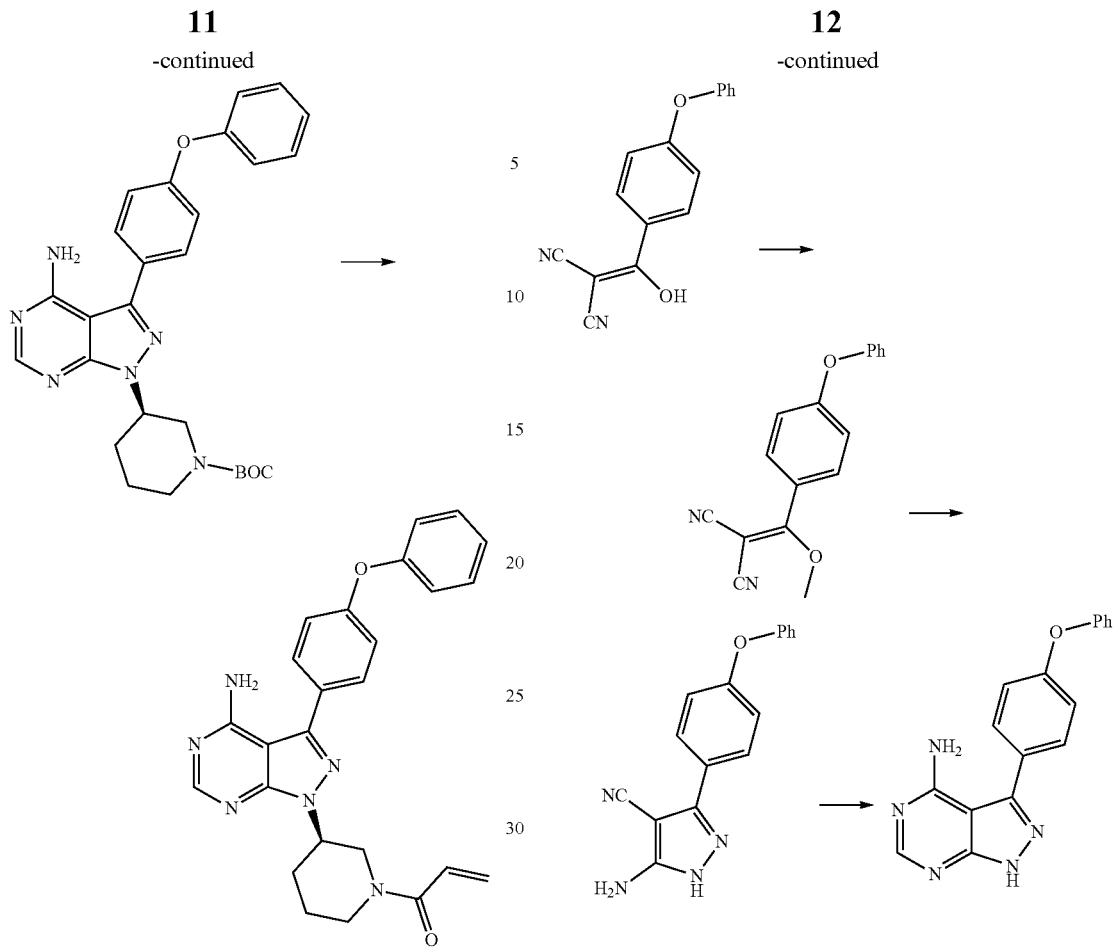

First, 4-amino-3-(4-phenoxyphenyl)-1H-pyrazole[3,4-d]pyrimidine may be prepared in accordance with procedures described in WO 2008/039218 (which is specifically incorporated herein by reference), for instance by converting 4-phenoxybenzoic acid to the corresponding acyl chloride (by using thionyl chloride), which latter product may be reacted with malononitrile to prepare 1,1-dicyano-2-hydroxy-2-(4-phenoxy-phenyl)ethene. The methoxy moiety is then methylated using trimethylsilyldiazomethane, and that methylated product is the treated with hydrazine hydrate to provide 3-amino-4-cyano-5-(4-phenoxyphenyl)pyrazole, which is reacted with formamide to provide 4-amino-3-(4-phenoxyphenyl)-1H-pyrazole[3,4-d]pyrimidine, as illustrated in the following scheme:

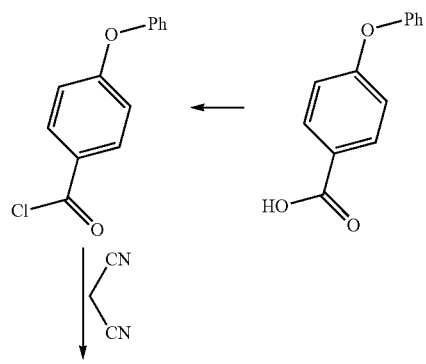

Thereafter, the 4-amino-3-(4-phenoxyphenyl)-1H-pyrazole[3,4-d]pyrimidine may have the requisite piperidinyl moiety introduced at the 1H-position (i.e. on the —NH of the pyrazole moiety). As indicated in the above scheme, this is done by means of a Mitsunobu reaction—more specifically by converting the hydroxy moiety of the Boc-protected 3-hydroxypiperidine-1-carboxylate to a better leaving group, thereby allowing a substitution reaction with the —NH moiety of the pyrazole (with inversion). Hence, the chirality of the hydroxypiperidine is translated into the product, which is then converted to the single enantiomer ibrutinib by Boc-deprotection and acylation with acryloyl chloride.

Other conversions (of products obtained by the process of the invention either directly or of further products resulting from downstream steps e.g. as may be described herein) may be performed in accordance with standard techniques and steps in the prior art, for instance, amide-forming reactions (in this instance, possible conditions and coupling reagents will be known to those skilled in the art), esterifications, nucleophilic substitutions reactions and aromatic nucleophilic substitution reactions.

EXAMPLES

The following examples are intended to illustrate the present invention and should not be construed as a limitation of the scope of the present invention.

Example 1

General Procedure for the Kinetic Resolution Screening

Scheme A

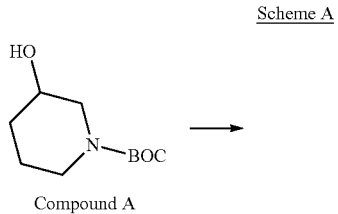

Compound A

→ and $R^1$ is hydrogen (i.e. rac-3-hydroxy-N-Boc-piperidine), referred to in Scheme A above as compound A (0.25 mmol, 0.25 mL). Finally toluene (0.5 mL) was added to bring the total reaction volume to 1 mL. The well plate was then sealed by a silicone sealing mat and placed on a shaker. The mixture was shaken at 500 rpm, at 40° C.

Samples were taken as follows: 50 µL of the reaction mixture was transferred to another plate, EtOAc (0.9 mL) was added and the plate centrifuged at 3000 rpm for 15 minutes. An aliquot of the supernatant (0.5 mL) was collected and diluted with EtOAc (0.5 mL) and analyzed by chiral gas chromatography ("GC"). Here conversion refers to the desired compound of formula (I) in which $R^2$ is Boc and $R^1$ is an acyl group as defined herein (and dependent on the acyl donor employed in the corresponding reaction)—referred to in Scheme A above as Compound B.

| Scale (mmol) | Enzyme (g/mol) | Base (equiv) | Acyl donor (equiv) | Solvent (L/mol) | Temp (° C.) | Reaction time (h) | Conversion (%) | ee (%) |
|---|---|---|---|---|---|---|---|---|
| 0.25 | AH06 (25) | Na$_2$CO$_3$ (1) | Iso-propenyl acetate (2) | Toluene (4) | 40 | 20 | 32.2 | 51.5 |
| 0.25 | AH09 (25) | Na$_2$CO$_3$ (1) | Iso-propenyl acetate (2) | Toluene (4) | 40 | 20 | 25.7 | 37.0 |
| 0.25 | AH17 (25) | Na$_2$CO$_3$ (1) | Iso-propenyl acetate (2) | Toluene (4) | 40 | 20 | 1.5 | 48.6 |
| 0.25 | AH19 (25) | Na$_2$CO$_3$ (1) | Iso-propenyl acetate (2) | Toluene (4) | 40 | 20 | 0.4 | 36.6 |
| 0.25 | AH24 (25) | Na$_2$CO$_3$ (1) | Iso-propenyl acetate (2) | Toluene (4) | 40 | 20 | 5.4 | 72.8 |
| 0.25 | Subtilisin (25) | Na$_2$CO$_3$ (1) | Iso-propenyl acetate (2) | Toluene (4) | 40 | 20 | 0.4 | 5.0 |
| 0.25 | SAV (25) | Na$_2$CO$_3$ (1) | Iso-propenyl acetate (2) | Toluene (4) | 40 | 20 | 4.1 | 3.2 |
| 0.25 | SAV (25) | Na$_2$CO$_3$ (1) | Isopropyl butyrate (2) | Toluene (4) | 40 | 20 | 9.1 | 96.6 |
| 0.25 | SAV (25) | Na$_2$CO$_3$ (1) | Trifluoroethyl acetate (2) | Toluene (4) | 40 | 20 | 13.3 | 99.1 |
| 0.25 | SAV (25) | Na$_2$CO$_3$ (1) | Trifluoroethyl butyrate (2) | Toluene (4) | 40 | 20 | 28.4 | 98.7 |
| 0.25 | SAV (25) | Na$_2$CO$_3$ (1) | Vinyl butyrate (2) | Toluene (4) | 40 | 20 | 45.3 | 96.6 |
| 0.25 | SAV (25) | Na$_2$CO$_3$ (1) | 3-F phenyl butyrate (2) | Toluene (4) | 40 | 40 | 37.4 | 98.5 |
| 0.25 | SAV (25) | Na$_2$CO$_3$ (1) | 4-F phenyl butyrate (2) | Toluene (4) | 40 | 40 | 35.1 | 97.8 |
| 0.25 | SAV (25) | Na$_2$CO$_3$ (1) | o-cresol 2-methoxy acetate (2) | Toluene (4) | 40 | 40 | 6.8 | 100 |
| 10 | SAV (25) | Et$_3$N (1) | Vinyl butyrate (2) | MeTHF (1) | 30 | 50 | 47.6 | 97.6 |
| 10 | SAV (25) | DIPEA (1) | Vinyl butyrate (2) | tert-amyl alcohol (1) | 30 | 50 | 34.5 | 100 |

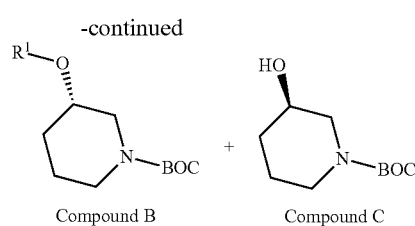

Compound B + Compound C

Kinetic resolution screenings were carried out in 96-well plates on 0.25 mmol scale, Enzyme (25 g/mol) was weighed and placed in each well along with Na$_2$CO$_3$ (1 equiv; compared to the starting material "Compound A"). Stock solutions (0.25 mL) of the corresponding acyl donors (2 equiv) in toluene were then added, followed by stock solutions of the compound of formula (II) in which $R^2$ is Boc In the above table, in order to measure ee and conversion, the ee is based on the ratio of the areas for the two possible enantiomers, i.e. in this case, compound B and its enantiomer. The conversion is the ratio of the sum of the two enantiomers of Compound B divided by the sum of the two enantiomers of the starting material Compound A, multiplied by the relative response factor (and hence refers to percentage conversion in which, in this case, refers generally to conversion of Compound A to Compound B plus its enantiomer).

General Procedure for the Large Scale Reactions:

A 100 mL reactor was charged with rac-3-hydroxy-N-Boc-piperidine, i.e. Compound A (80 mmol, 16.10 g), savinase enzyme (25 g/mol, 2.00 g) and toluene (80 mL). DIPEA (80 mmol, 16 mL) and vinyl butyrate (1.1 eq, 11 mL) were finally added to the reaction mixture. The reaction was worked up after 42 hours. The mixture was filtered. The mother liquor was extracted with acidic water (pH<2, 3×100 mL). The organic layer was then dried over MgSO₄ and concentrated in vacuo. Flash column chromatography (heptane:EtOAc, 95%→90%→40% heptane) was used (TLC $R_f$ "Compound C": 0.7, $R_f$ "Compound B" in which $R^1$ is —C(O)—(CH₂)₂CH₃": 0.2 in 7:3 heptane:EtOAc). This gave (S)-"butyrate" Compound B (3-(S)-butyroxy-N-Boc-piperidine) as a colorless oil (9.29 g, 31.7% yield 97.8% ee) and the (R)-alcohol Compound C as a colorless oil that solidified on standing (11.06 g, 51.0% yield 61.8% ee).

Succinic Anhydride Work Up Modification:

The general procedure for the large scale EasySampler reactions was used. The reaction mixture was filtered after 44 hours, the filtrate was transferred to a clean 100 mL EasyMax reactor, succinic anhydride (4.80 g, 48 mmol) was added, along with 4-dimethylaminopyridine (0.24 g, 2 mmol). The reaction mixture was then heated at 50° C. for 18 hours. The mixture was then transferred to a separation funnel, water (25 mL) and NaHCO₃ (sat., 25 mL) were added and the layers separated. The aqueous layer was extracted with toluene twice (50 mL and 30 mL). The organic layers were combined, extracted with HCl (1 M, 100 mL), and dried over MgSO₄. Subsequent removal of volatiles in vacuo gave (S)-"butyrate" Compound B as a brown liquid (8.056 g, 50.1% yield, 97.5% ee).

Further Example A: Ibrutinib (or a salt thereof) is prepared by preparing an intermediate using any of the processes steps described in Example 1, following by conversion to ibrutinib (or a salt thereof).

Further Example B: A pharmaceutical composition is prepared by first preparing ibrutinib (or a salt thereof) as per Example 2, and then contacting ibrutinib (or a salt thereof) so obtained with a pharmaceutically acceptable carrier, diluent and/or excipient.

The invention claimed is:

1. A process for preparing a compound of formula (I):

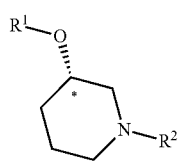
(I)

in an enantio enriched form, wherein:
$R^1$ is hydrogen,
$R^2$ is tert-butyloxycarbonyl (BOC);
\* is a chiral centre of an(S) configuration;
the process comprising Savinase enzymatic kinetic resolution of a compound of formula (II):

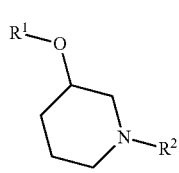
(II)

in the presence of (i) an acyl donor that is vinyl butyrate or o-cresol methoxy acetate, (ii) a solvent that is toluene, methyl-tetrahydrofuran, or tert-amyl alcohol, and (ii) an inorganic base that is sodium carbonate (Na₂CO₃), triethylamine (Et₃N), or N,N-diisopropylethylamine (DIPEA).

2. The process of claim 1, wherein the acyl donor is vinyl butyrate.

3. The process of claim 1, wherein at least one equivalent of acyl donor is used compared to the compound of formula (II).

4. The process of claim 3, where two equivalents of acyl donor are employed compared to the compound of formula (II).

5. The process of claim 1, wherein the Savinase is AH24, AH06, AH09, AH 17, AH 19, AH24, and/or Subtilisin.

6. The process of claim 1, wherein the process is performed at a temperature of between 25 and 40° C.

7. The process of claim 1, wherein the resolution is a dynamic kinetic resolution, performed in the presence of a racemisation catalyst.

8. The process of claim 7, wherein the racemisation catalyst is selected from the group consisting of compound I, compound II, compound III, and compound IV:

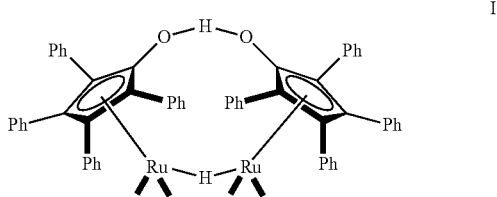
I

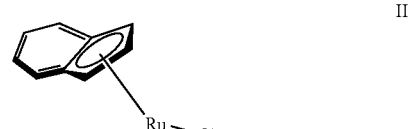
II

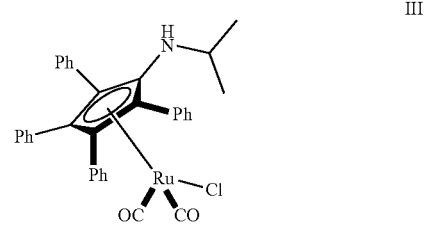
III

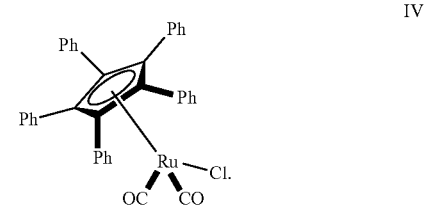
IV

9. The process of claim 1, further comprising:
separation/isolation of the compound of formula (I); and
conversion of the compound of formula (I) to ibrutinib.

10. The process of claim 9, comprising converting the compound of formula (I) to ibrutinib using the following steps:

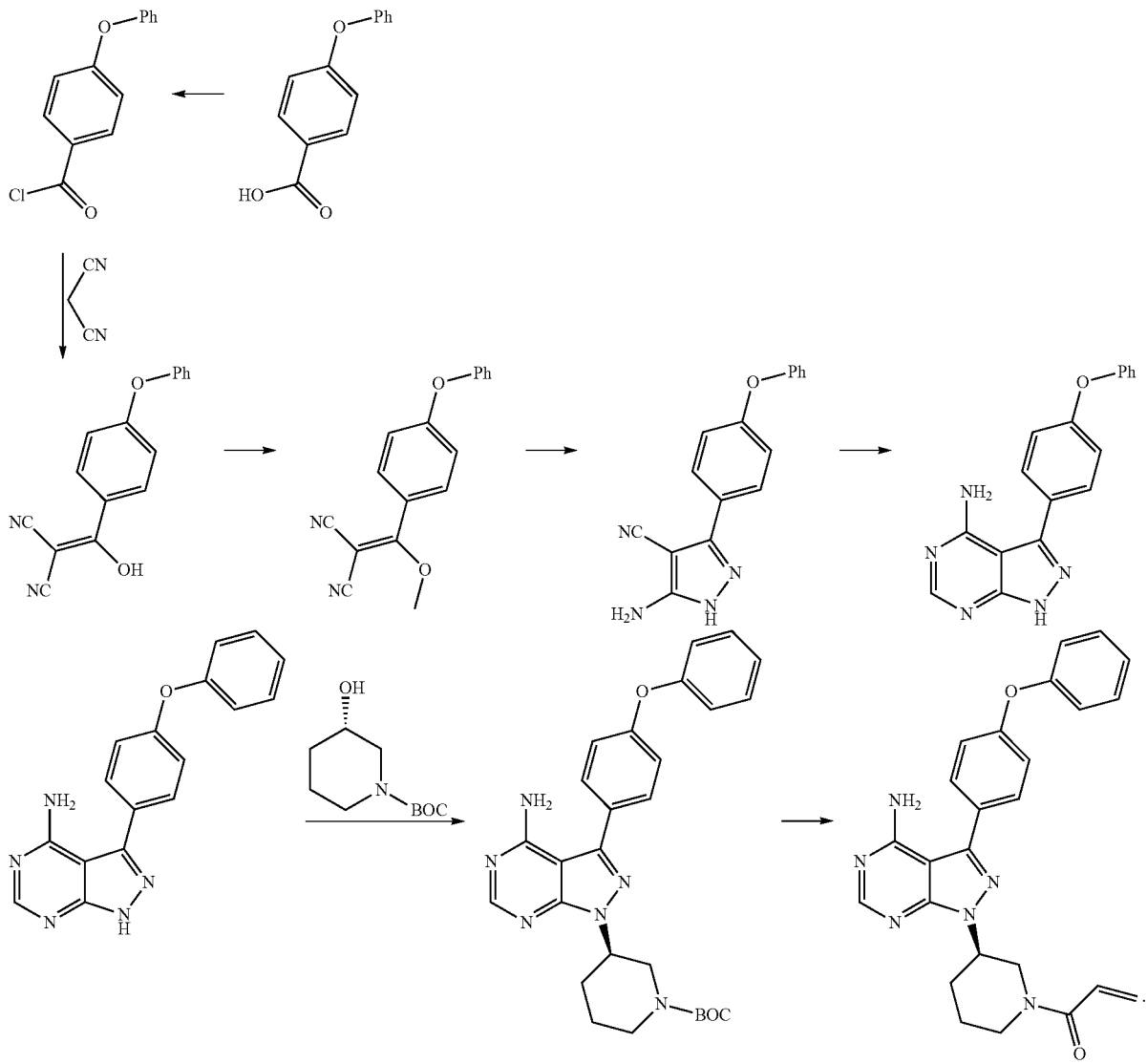

11. The process of claim 1, wherein the inorganic base is sodium carbonate.

12. The process of claim 1, wherein the solvent is toluene.

13. The process of claim 6, wherein the temperature is between 25 and 35° C.

14. The process of claim 13, wherein the temperature is 30° C.

15. The process of claim 1, wherein the solvent is methyl-tetrahydrofuran.

16. The process of claim 1, wherein the solvent is tert-amyl alcohol.

17. The process of claim 1, wherein the inorganic base is triethylamine.

18. The process of claim 1, wherein the organic base is N-diisopropylethylamine.

* * * * *